Figure 1:
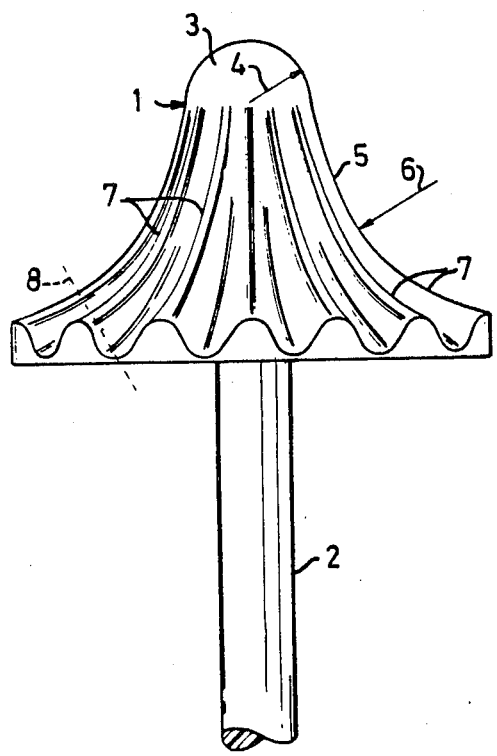

United States Patent [19]

Stenkvist

[11] 4,448,205
[45] May 15, 1984

[54] DEVICE FOR TAKING SAMPLES OF CELLS FROM THE CERVIX UTERI

[76] Inventor: Björn G. Stenkvist, Döbelnsgatan 13, S-752 37 Uppsala, Sweden

[21] Appl. No.: 355,589
[22] PCT Filed: Jun. 30, 1981
[86] PCT No.: PCT/SE81/00198
    § 371 Date: Feb. 18, 1982
    § 102(e) Date: Feb. 18, 1982
[87] PCT Pub. No.: WO82/00090
    PCT Pub. Date: Jan. 21, 1982

[30] Foreign Application Priority Data

Jul. 8, 1980 [SE] Sweden .............................. 8005022

[51] Int. Cl.³ .............................................. A61B 10/00
[52] U.S. Cl. ...................................... 128/749; 128/304; 128/757
[58] Field of Search ............... 128/304, 749, 751, 756, 128/757, 758, 752, 755, 737, 778, 305.1, 310, 92 E

[56] References Cited

U.S. PATENT DOCUMENTS

| | | | |
|---|---|---|---|
| 2,514,665 | 7/1950 | Myller | 128/757 |
| 3,472,230 | 10/1969 | Fogarty | 128/304 X |
| 3,540,432 | 11/1970 | Ayre | 128/758 |
| 3,796,211 | 3/1974 | Kohl | 128/757 X |
| 3,913,564 | 11/1975 | Freshley | 128/759 |

Primary Examiner—Henry J. Recla
Assistant Examiner—Christine A. Fukushima
Attorney, Agent, or Firm—Stevens, Davis, Miller & Mosher

[57] ABSTRACT

Device for taking samples of cells from the cervix for preparation and testing of whether abnormal cells are present in the sample, the device consisting of a conical body (1) with a concave undulated lateral surface (5) and a hemispherical tip (3), the undulated surface extending from the base of the conical body to the hemispherical tip. The base radius of the cone is 5-15 mm. The radius of the hemispherical tip is 2-4 mm. The radius of the circular arc defining the concave lateral surface (5) of the conical body (1) is less than 50 mm. The undulated lateral surface defines in cross section taken through an imaginary conical section normal to the surface, and the apex of which lies on the longitudinal axis of the conical body, a sine curve with decreasing wavelength and amplitude along the circular arc approaching the tip. The amplitude and wavelength are 1.5-5 mm at the base of the conical body. The device is suitably supplemented with a test tube (12) and a screw cap (13) fitted thereto, through which the rod (11) passes.

3 Claims, 2 Drawing Figures

DEVICE FOR TAKING SAMPLES OF CELLS FROM THE CERVIX UTERI

The present invention relates to an instrument for clinical sampling of exfoliated cells from the cervix.

Cytological tests of cell samples are now quite extensive and have proved to be an exceptional means for diagnosing cell changes in the area around the portio-cervix and endocervical canal. Such tests are made in great number and it is not uncommon that entire age groups of women within a district are tested.

Cell samples from said area reveal cell changes with a reliability of about 95% and of the positive results, 20-25% are pre-cancerous. A positive result in this test usually results in an operation, e.g. a so-called scraping or use of a coned instrument. The result of such treatments is usually good and warrants extensive taking of samples from healthy women in certain age groups.

The samples are usually taken with a curette or similar instrument by scraping cells from the mouth of the cervix. The sample is smeared directly on a slide, is fixed and transported to a cytological laboratory. At the laboratory the sample is prepared for microscopic examination by suitable dyeing. Finally the dyed cell sample is examined under the microscope, and the presence of atypical cells is noted and reported. The work with microscopic examination is demanding and time-consuming. The total cost for a sample is 50-100 Swedish Kronor (1980).

Consequently intensive development work is in progress to make the work with cytological samples less expensive and simpler. In order to facilitate the work with the evaluation of samples under the microscope, several different systems are being developed for automatic evaluation of cells in cell samples as normal or atypical. Algorithms have been developed for automatic evaluation and even the development of commercial systems is fairly well along.

In order to evaluate cells automatically, it is very important that the samples contain a sufficient number of cells and that the cell sample actually be taken so that any cell changes are actually represented in sufficient amounts.

When taking clinical samples from the cervix, the person taking the sample usually insets a speculum into the vagina, and a curette is then inserted via the speculum to the cervix and is rotated in the mouth of the cervix. It is however difficult even for an experienced taker of samples to always get a representative sample. A number of different sampling instruments have been developed, among which we might mention the one described in U.S. Patent Specification No. 2 514 665.

According to this patent, an instrument is used with a conical body at its upper end provided with a cutting edge which scrapes or cuts off material from the cervix when the instrument is rotated in the cervical canal.

According to another U.S. Patent No. 2 839 051, a device is revealed which cuts tissue from the cervix with a razorblade edge, said device comprising a conical body designed to penetrate into the cervical canal and center said razorblade edge in relation to the cervix. The cone is provided with cutting teeth which cuts off tissue in the cervical canal.

U.S. Pat. No. 3 540 432 shows an instrument consisting of a rod with a conical end provided with ribs for sampling in the cervix. Somewhat surprisingly, the instrument is said to be capable of self-use. U.S. Pat. No. 3 881 464 shows an instrument for sampling in the cervix consisting of a brush made with a spirally turned wire. The brush appears to require very careful handling in order not to cause injury.

None of the previously known sampling instruments is suitable for large series of tests, in which even people with less extensive training will be able to take samples clinically and at the same time see to it that the sample taken is sufficiently representative for reliable automatic evaluation.

Even for experienced samplers it has proved difficult to insert the previously known sampling instruments into the cervical canal without causing injury. It is also known that cell changes can be situated at different points in the cervical canal. Table 12 in "Diagnostic Cytology" by Leopold Kass, New York (1979) reveals that the portio-cervix and the cervical canal have a very individual appearance in different women and furthermore the appearance varies with age and whether or not the women has borne children.

The new instrument according to the invention solves at the same time several of the problems with sampling in the portio-cervix and cervical canal.

The new device for sampling of cells from the cervix is characterized in that it consists of a rod which serves as a handle when taking samples, and a conical body placed on the rod with a concave undulated lateral surface and a hemispherical tip, said undulated surface extending from the base of the conical body to the hemispherical tip, the base radius of the cone being 5-15 mm, the radius of the hemispherical tip being 2-4 mm, the radius of the arc defining the concave lateral surface of the conical body being less than 50 mm and the undulated lateral surface approximately defining, in cross-section taken through an imaginary conical section to said surface and the apex of which lies on the longitudinal axis of the conical body, a sine curve with decreasing wavelength and amplitude along the circular arc approaching the tip, the wavelength and amplitude being between 1.5 and 5 mm at the base of the cone.

The new device can be inserted with almost complete security into the vagina via a speculum and the sampler can push the conical body without difficulty against the cervix and place the hemispherical tip in the mouth of the cervical canal. The device is suitably made as a unit in which a vessel, suitably a tubular vessel, a sealing device, suitably a screw cap, is arranged around the rod and with suitable surfaces for marking the sample. A preferred embodiment is revealed in the accompanying figures.

Figure 2:
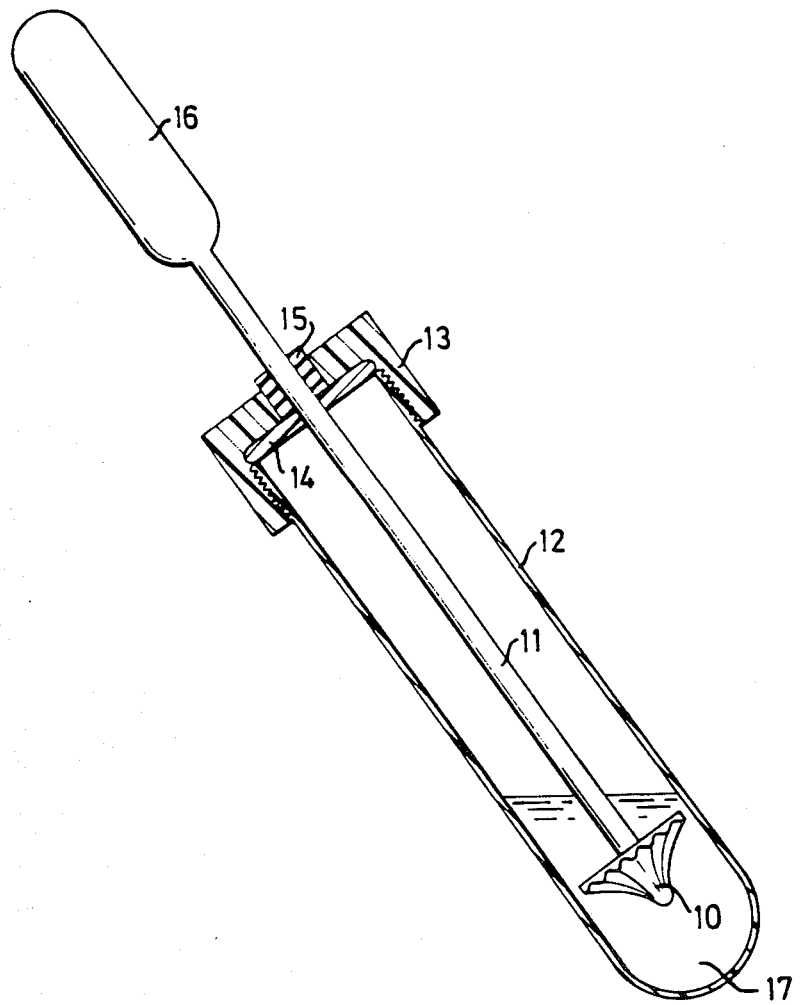

The invention will now be described with reference to the accompanying drawing, in which FIG. 1 shows the conical body and FIG. 2 shows a complete sampling set according to the invention.

FIG. 1 shows a conical body 1 with a rod 2 (not shown completely here). The body 1 consists of a tip 3 with hemispherical shape and with a radius according to the arrow 4. The lateral surface 5 of the conical body is concave along the circular arc with a radius indicated by the arrow 6. The edge surface is also undulated with waves 7 of approximately sine shape. The sine shape is revealed if the cone is cut circularly by rotating a section along the dashed line 8 perpendicular to the circular arc surface.

FIG. 2 shows the conical body 10, the rod 11 functioning as a handle, a test tube 12 with a screw cap 13 provided with a packing 14 and a sealed lead-in 15 for the rod 11. The rod 11 is provided at its upper end with a portion 16 suited for labelling the sample with a name etc. The figure also indicates that the tube 12 is filled with fixing solution 17 which surrounds the conical body and forms a slurry of exfoliated cells.

I claim:

1. Device for taking samples of cells from the cervix, characterized in that it consists of a rod, a conical body having a concave undulated lateral surface and a hemispherical tip, said rod connected to the base of said conical body and extending coaxially with the longitudinal axis thereof, said undulated surface extending from the base of the conical body to the hemispherical tip, the base radius of the cone being 5-15 mm, the radius of the hemispherical tip being 2-4 mm, the radius of the arc defining the concave lateral surface of the conical body being less than 50 mm and the undulated lateral surface approximately defining in cross-section taken through an imaginary conical section normal to said surface and the apex of which lies on the longitudinal axis of the conical body, a sine curve with decreasing wavelength and amplitude along the circular arc approaching the tip, the wavelength and amplitude being between 1.5 and 5 mm at the base of the cone.

2. Device according to claim 1, characterized in that the rod is provided with a sealing means so that the conical body can be inserted into a vessel, which is sealed by the sealing means.

3. Device according to claim 2, characterized in that the sealing means consists of a screw cap fitting into a tube provided with threads.

* * * * *